United States Patent [19]

Gocho

[11] Patent Number: 4,754,414
[45] Date of Patent: Jun. 28, 1988

[54] REAGENT MANAGING SYSTEM

[75] Inventor: Nagahiro Gocho, Hachioji, Japan

[73] Assignee: Olympus Optical Co., Ltd., Tokyo, Japan

[21] Appl. No.: 699,947

[22] Filed: Feb. 8, 1985

[30] Foreign Application Priority Data

Feb. 13, 1984 [JP] Japan ................... 59-22944

[51] Int. Cl.$^4$ ................. G06F 15/20; G01N 33/16
[52] U.S. Cl. .................... 364/497; 422/62
[58] Field of Search ............... 364/497–499, 364/707, 502, 900 MS File, 403; 422/62–67

[56] References Cited

U.S. PATENT DOCUMENTS

| | | | |
|---|---|---|---|
| 4,254,460 | 3/1981 | Achter et al. | 364/497 X |
| 4,281,387 | 7/1981 | Kraft et al. | 364/497 |
| 4,419,734 | 12/1983 | Wolfson et al. | 364/403 X |
| 4,459,265 | 7/1984 | Berglund | 364/497 |
| 4,483,927 | 11/1984 | Takekawa | 364/497 X |
| 4,523,295 | 6/1985 | Zato | 364/900 |
| 4,639,875 | 1/1987 | Abraham et al. | 364/403 X |

Primary Examiner—Gary V. Harkcom
Assistant Examiner—H. R. Herndon
Attorney, Agent, or Firm—Stevens, Davis, Miller & Mosher

[57] ABSTRACT

A plurality of reagents for use in an automatic chemical analyzer are managed by initially setting into a random access memory amounts of reagents initially set in the analyzer and by changing the amounts of reagents every time the reagents are used. When an electrical power supply is switched off, the amounts of reagents stored in the random access memory are transferred into a non-volatile memory, and when the electric power supply is switched on again, the amounts of reagents stored in the non-volatile memory are transferred into the random access memory. Therefore, it is no more necessary for a user to set amounts of reagents remained in the analyzer every time the electric power supply is switched on.

16 Claims, 2 Drawing Sheets

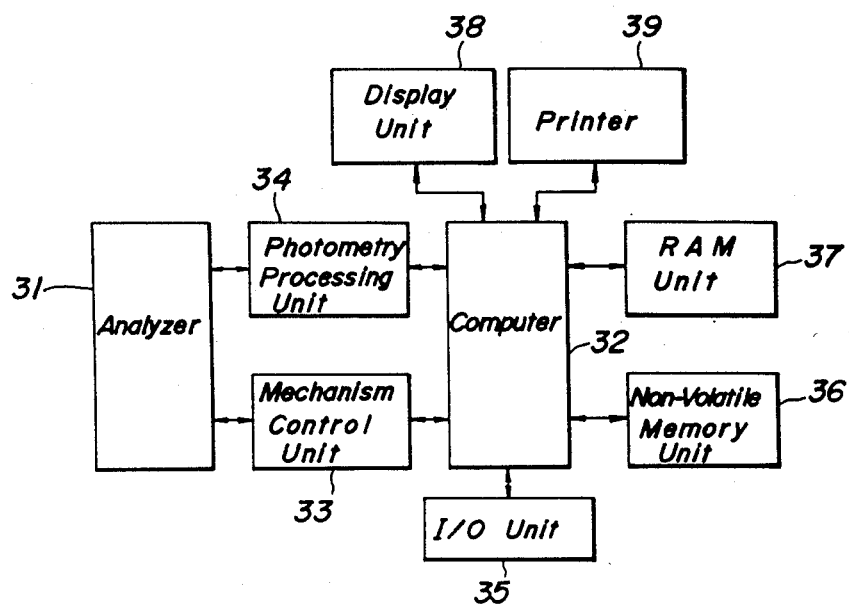
FIG_2
FIG_3

REAGENT MANAGING SYSTEM

BACKGROUND OF THE INVENTION

The present invention generally relates to an automatic chemical analysis, and more particularly to a system for managing liquids such as reagents and buffer solution for use in an automatic chemical analyzer.

In an automatic chemical analyzer, one or more reagents are added to a sample liquid to effect a reaction and a reacted solution is tested by a colorimeter or an ion sensitive electrode device. At present, in accordance with the technological progress of analyzer systems, it has been required to make an amount of a reagent as small as possible. For instance, in case of testing a serum, an amount of the sample serum for a single test item is about 5 to 25 $\mu l$ and an amount of a reagent is about 50 to 200 $\mu l$. Further, in order to simplify the maintenance, the reagent is stored in a refrigerator provided in the analyzer and can be kept therein for more than one week. In some analyzers, a reagent of high concentration is stored in a reagent tank and a diluted reagent is delivered into a reaction vessel. Then the number of tests which can be performed by the reagent contained in the tank can be increased by a factor which corresponds to a dilution ratio.

Formerly it was common to set required reagents in an analyzer at a start of analyzing work every day, but presently an exchange or supplement of reagents is effected once a week due to the fact that a required amount of the reagent has been decreased materially and the reagent has been hardly damaged for a long time. Then, there has arisen another problem that the management of the reagents might be forgotten by a user. In order to avoid such a problem, there has been proposed in Japanese patent application laid-open publication No. 82,769/82 an apparatus for managing reagents set in an automatic chemical analyzer. In this known apparatus residual amounts of reagents contained in reagent tanks are automatically calculated from signals supplied from a liquid level detector and signals representing distances over which a nozzle of a reagent pipetter descends in respective tanks, and calculated residual amounts of the reagents are displayed on a screen of a cathode ray tube. In this known reagent managing apparatus, in order to obtain a high reliability it is necessary to make high the precision of the liquid level detector and the mechanism for moving the nozzle up and down including, for instance a pulse motor. As a result, it is apparent that the liquid level detector and the reagent pipetter become complicated in construction and expensive in cost.

SUMMARY OF THE INVENTION

The present invention has for its object to provide a system for managing one or more reagents set in an automatic chemical analyzer, which can manage the reagents with a high reliability by utilizing a computer, an input device for the computer and a reagent delivery device and which does not need special mechanisms and expensive driving mechanisms.

According to the invention, a system for managing one or more reagents set in a reagent storing section of an automatic chemical analyzer comprises:

means for setting values representing amounts of respective reagents initially set in the reagent storing section;

first storing means comprising a random access memory for storing the values entered by said setting means;

means for displaying the values stored in said first storing means; and second storing means including a non-volatile memory for storing the values stored in the first storing means; whereby each time an aliquot of a reagent set in the reagent storing section is delivered into a reaction vessel, a value related to this reagent is changed by one unit and a thus changed value is stored in the first storing means and is displayed on the displaying means.

In most automatic chemical analyzers to which the present invention is applied, there have been already provided a memory, computer and keyboard, and thus the system according to the invention can be practiced easily by slightly modifying them. Therefore, the present invention can be practiced in a very simple and economical manner.

In the present invention, when an electric power supply is switched off due to the completion of analysis or for any other reason, the second storing means has stored the values representing residual amounts of the reagents in a non-volatile manner. The values thus stored in the second storing means are readout into the first storing means at a time when the electric power supply is switched on again. Therefore, the residual amounts of the reagents are always displayed on the displaying means without entering again the residual amounts of the reagents every time the analyzer is operated. Thus, the management of the reagents can be effected easily and precisely. Moreover, by comparing the stored values with threshold values it is possible to produce an alarm or automatically stop the analyzer when any one of the residual amounts of the reagents is decreased below a predetermined volume corresponding to the relevant threshold value.

BRIEF DESCRIPTION OF THE DRAWINGS

FIG. 2 is a block diagram illustrating an embodiment of the reagent managing system according to the invention; and FIG. 3 is a plan view depicting an example of an image displayed on a display screen.

DESCRIPTION OF THE PREFERRED EMBODIMENTS

Figure 1:
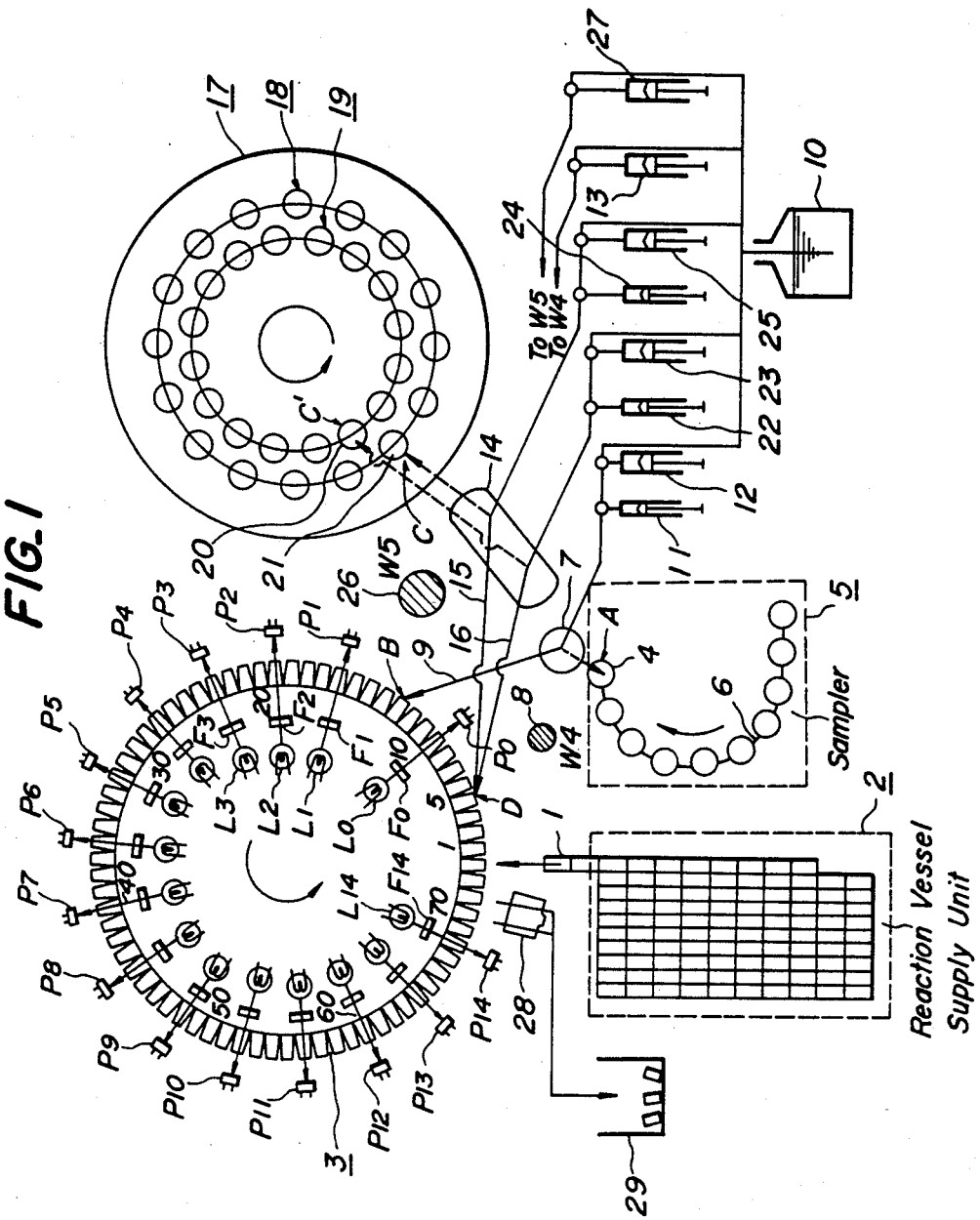
FIG. 1 is a schematic view showing an embodiment of the automatic chemical analyzer to which the present invention is applied.

FIG. 1 is a schematic view showing an embodiment of the automatic chemical analyzer to which the reagent managing system according to the invention is applied. The analyzer is of a so-called sequential multi type. Reaction vessels 1 are supplied from a reaction vessel supply unit 2 to a reaction lane 3 one by one in each analyzing period. The reaction vessel 1 has a capacity of about 2 ml and is made of transparent material such as plastics. For instance, a plastic curvette may be advantageously used as the reaction vessel. In the present embodiment, the reaction vessel 1 is wasted, but may be repeatedly used after washing.

Sample vessels 4 containing samples to be tested are supported by a sample vessel holder 6 such as a snake chain in a sampler 5 and the sample vessel holder 6 is driven in accordance with one or more test items to be effected for respective samples. A given amount of a sample contained in a sample vessel 4 just situating at a sample sucking position A in the sampler 5 is taken out by a sample delivery device 7 and the sample aliquot thus taken is delivered into a reaction vessel which is just in a sample delivery position B on the reaction lane 3. After the delivery of the sample, both outer and inner walls of a probe 9 of the sample delivery device 7 are washed and cleaned in a probe washing vessel 8. The analyzer further comprises a container 10 for containing a diluting liquid, e.g. a distilled water for use in washing and diluting samples, a sample delivery syringe pump 11 and a sample diluting syringe pump 12.

Now the operation of the sample delivery will be explained. At first, the sample delivery probe 9 is moved downwards at the position A in the sampler 5 and sucks therein a given amount of a sample contained in a sample vessel 4 by means of the sample delivery syringe pump 11. Then the probe 9 is moved upwards and is shifted into the sample delivery position B in the reaction lane 3. By this time, a given amount of the diluting liquid contained in the container 10 has been sucked in the syringe pump 12. Then, the sample aliquot and diluting liquid aliquot are discharged successively into a reaction vessel 1 situating at the sample delivery position B. After that, the probe 9 is moved into the washing vessel 8 and the diluting liquid is flowed through the probe 9 into the washing vessel 8 by means of the sample delivery syringe pump 11 to wash the inner wall of the probe. Then, the diluting liquid is supplied into the washing vessel 8 by means of the washing syringe pump 13 to wash the outer wall of the probe 9. After washing, the probe 9 is filled with the diluting liquid by driving the sample diluting syringe pump 12 to prepare for a next sample delivery.

Now the mechanism for delivering the reagent will be explained. A reagent delivery mechanism 14 comprises first and second reagent probes 15 and 16. First and second reagent tank groups 18 and 19 are concentrically arranged in a reagent storage unit 17. The first reagent probe 15 is connected to a first reagent delivery syringe pump 22 and a first reagent diluting syringe pump 23, and the second reagent probe 16 is coupled with a second reagent delivery syringe pump 24 and a second reagent diluting syringe pump 25. The first and second reagent tank groups 18 and 19 of the reagent storage unit 17 are separately rotated by a suitable driving mechanism not shown and any desired reagent tanks of the groups 18 and 19 corresponding to a test item to be performed can be indexed at reagent sucking positions C and C', respectively under the control of a computer. The reagents sucked in the probes 15 and 16 are discharged into a single reaction vessel 1 at a reagent delivery position D. There is further provided a washing vessel 26 and a syringe pump 27 for supplying the diluting liquid to the vessel 26, so that the reagent delivery probes 15 and 16 are washed and cleaned in the same manner as that explained above in case of washing the sample delivery probe 9.

There are arranged fiften photosensors $P_0$ to $P_{14}$ along the periphery of the reaction lane 3. The photosensor $P_0$ is provided at a downstream position in the reaction lane 3 with respect to the reagent delivery position D and effects a photometry for a reagent blank contained in a reaction vessel 1. The remaining photosensors $P_1$ to $P_{14}$ are arranged at downstream positions with respect to the sample delivery position B and are separated from each other by four positions of the reaction lane 3. When the reaction vessel supply position is assumed to be a first position of the reaction lane 3, the photosensor $P_0$ is arranged at ninth position and the photosensors $P_1$ to $P_{14}$ extend from sixteenth position to a sixty eighth position as illustrated in FIG. 1. After given one or more reagents have been delivered into a reaction vessel 1 at the position D, a sample is delivered in the relevant reaction vessel at the position B to form a test liquid. The test liquid thus formed is stirred by a suitable agitator not shown to promote a reaction. The test liquid in the reaction vessel is photometered successively by the photosensors $P_1$ to $P_{14}$ and a change of an absorption of the test liquid is measured. In the present embodiment, the reaction lane 3 is rotated in a stepwise manner at a period of nine seconds and thus each test liquid is measured by the photosensors $P_1$ to $P_{14}$ at a period of thirty six seconds to obtain fourteen measured values in all.

Within the reaction lane 3 are arranged light sources $L_0$ to $L_{14}$ and filters such as interference filters $F_0$ to $F_{14}$ at positions corresponding to the photosensors $P_0$ to $P_{14}$, respectively. Each filter can select any one of ten wavelengths in accordance with a test item to be analyzed.

There is further provided a device 28 for removing the reaction vessels from the reaction lane 3 after the measurement and removed reaction vessels are discharged into a waste box 29.

FIG. 2 is a block diagram illustrating an embodiment of the reagent managing system according to the invention for controlling the operation of the analyzer shown in FIG. 1. In FIG. 2 the analyzer is generally shown by a block 31. Various motors, syringes, solenoids, light sources, etc. in the analyzer 31 are controlled by a mechanism control unit 33 which is operated by commands supplied from a computer 32, so that the analyzer 31 is driven in a manner explained above to effect the colorimetric analysis for successive samples.

Output signals from the photosensors $P_0$ to $P_{14}$ provided in the analyzer 31 are supplied to a photometry processing unit 34 comprising multiplexer, amplifier, A/D converter, etc. The photometry processing unit 34 derives information about test items, absorption values and so on which are then supplied to the computer 32.

To the computer 32 is connected an input unit 35 comprising a keyboard for setting or entering into the computer 32 analytic conditions, test items, amounts of reagents which are initially set in the analyzer 31, threshold values for alarm, etc. There is provided a non-volatile memory unit 36 for storing various data in a non-volatile manner even when a main power supply is switched-off at the end of the analysis or the main power supply is automatically broken down due to malfunction. In the present embodiment, the non-volatile memory unit 36 comprises a floppy disc storage, but may utilize hard disc storage, bubble memory, core memory, battery backed-up CMOS.RAM, etc. There is further arranged a random access memory unit 37 for storing data and programs which are required for effecting control and calculation. The programs may be permanently stored in a programmable read only memory. A display unit 38 comprises a cathode ray tube on which various kinds of outputs processed by the computer 32, e.g. amounts of reagents for respective test items, alarm, message, operation menu, etc. Some of data displayed on the display unit 38 may be recorded on a record sheet by means of a printer 39.

Now the operation of the analyzer 31 will be explained in detail.

Sample vessels 4 containing samples to be tested are first set to the sample vessel holder 6 in the sampler 5.

Then, test items to be effected for these samples are entered into the computer 32 by means of the input unit 35. These data are stored in the memory 37 via the computer 32. Then a start switch is made on to initiate the analyzing operation. The sampler 5 is controlled by the mechanism control unit 33 under the control of the computer 32 and a first sample vessel is fed into the sample sucking position A. The relevant sample vessel is stopped at the position A for a time period corresponding to the number of test items to be analyzed for a sample contained in the relevant sample vessel. In a similar manner, successive sample vessels are fed into the sample sucking position A in a stepwise manner. At the same time the reaction vessel supply unit 2 is also controlled by the mechanism control unit 33 and reaction vessels are successively supplied into the reaction lane 3 at the period of nine seconds. The reaction lane 3 is intermittently rotated in the anti-clockwise direction at the period of nine seconds to feed the reaction vessels in a stepwise manner.

After a reaction vessel has been supplied to the reaction lane 3 at a first position, when the relevant reaction vessel is fed into the reagent delivery position D at a fifth position, the reagent tank groups 18 and 19 of the reagent storage unit 17 are rotated by the mechanism control unit 33 and reagent tanks 20 and 21 containing reagents corresponding to a test item which is to be effected to a sample which will be delivered in the relevant reaction vessel at the position B, are indexed at the reagent sucking positions C and C'. Then predetermined amounts of the reagents in the tanks 20 and 21 are sucked into the probes 15 and 16 and the sucked reagents are delivered together with a given amount of the diluting liquid into the relevant reaction vessel at the reagent delivery position D. It should be noted that in case of effecting a test item requiring only one reagent, either one of the probes 15 and 16 of the reagent delivery unit 14 is remained inoperative.

In the same manner as explained above, required reagents corresponding to test items for successive samples are delivered together with a given amount of the diluting liquid into reaction vessels which are successively fed into the reagent delivery position D under the control of the computer 32.

After one or more reagents have been delivered into the reaction vessel, the reagent blank is measured at the ninth position of the reaction lane 3 by means of the first set of photosensor $P_0$, light source $L_0$ and filter $F_0$. Then, at the sample delivery position B, i.e. at the fifteenth position of the reaction lane 3, a given amount of sample is delivered together with a given amount of the diluting liquid into the reaction vessel.

In the manner explained above, successive samples contained in the sample vessels 4 indexed at the position A of the sampler 5 are delivered into successive reaction vessels 1 indexed at the position B in the reaction lane 3. Test liquids formed in the reaction vessels are photometered by one or more photosensors corresponding to required test items. After the measurement, the reaction vessels 1 fed into the seventieth position of the reaction lane 3 are successively removed from the reaction lane 3 by means of the reaction vessel removing unit 28.

Photometered signals supplied from the photosensors $P_0$ to $P_{14}$ are converted into digital signals by the photometry processing unit 34 and the thus converted digital signals are supplied to the computer 32. These signals are processed by the computer 32 separately for respective test liquids to derive absorption values of respective test liquids. Then variations in the absorption are calculated for respective test liquids and concentrations of substances contained in samples are calculated with the aid of calibration curve data which has been previously stored in the memory 37. The concentration values thus obtained are displayed on the display unit 38 and are printed out by the printer 39.

Next the management of the reagents contained in the reagent tanks of first and second reagent tank groups 18 and 19 in the reagent storage unit 17 will be explained.

It is now assumed that the reagent tanks are initially set in the reagent storage unit 17. Then, data representing amounts of reagents contained in respective reagent tanks is entered by operating the keyboard of the input unit 35 into the computer 32. The data may directly denote the amounts of reagents or may represent the numbers of tests which can be performed by the reagents contained in the reagent tanks. The number of tests is represented by a quotient obtained by dividing a total amount of a reagent by an amount of the reagent required for effecting a single test. In the present embodiment, the numbers of tests are entered into the computer 32 and are stored in a predetermined area of the memory 37. The numbers of tests are also stored in a predetermined area of the non-volatile memory unit 36. In the initial state, instead of entering the reagent amount data with the aid of the input unit 35, they may be stored in a floppy disc of the non-volatile memory unit 36. In such a case, there may be stored the numbers of tests which can be performed by the maximum amounts of reagents contained in the reagent tanks. In this case, the reagent amount data may be transferred into the memory 37 in the initial condition. It should be noted that the reagent tanks have to be fully filled with the reagents when they are initially set in the reagent storage unit 17.

After the initial setting, the data values representing the reagent amounts are always stored in the non-volatile memory 36 and when the power supply to the analyzer is switched-on, the data values stored in the non-volatile memory unit 36 are readout and transferred into the random access memory unit 37 by means of the computer 32.

In the manner explained above, in the given area of the memory unit 37 are stored the data values about the amounts of the reagents stored in the reagent storage unit 17. The data values always represent the numbers of tests which can be performed by the reagents now stored in the reagent storage unit 17. When the reagent delivery device 14 of the analyzer 31 is operated to deliver a given amount of a reagent, the number of tests related to the relevant reagent is decreased by one, and then the number of tests stored in the memory unit 37 is replaced by the number of tests reduced by one. For instance, when a test item is GOT using first and second reagents and each of the numbers of tests of the initially set reagents is 600, the numbers of tests of these reagents are changed to 599 after GOT is measured for a single sample. Further, when a next test item is GPT using a third reagent whose initial number of tests is 450, the number of tests of the relevant third reagent is changed from 450 to 449 after the GPT analysis has been effected for the next sample. In the manner explained above, after an analysis has been performed, the numbers of tests for one or more reagents relating to the relevant analysis are reduced by one.

FIG. 3 shows an example of an image displayed on the display unit 38. A column 41 indicates the numbers of test items, 42 names of test items, 43 the numbers of tests of the reagents belonging to the first reagent tank group 18, 44 the numbers of tests of the reagents in the second reagent tank group 19 and a column 45 represents alarm threshold values which will be explained later. In the second column 43, 20 indicates that the number of tests which will be able to be performed by the remaining reagent has been reduced to the alarm threshold value 20 and thus a figure "20" is displayed in a reversed manner. As can be seen from FIG. 3, only test items GOT, GPT, LDH and AMY need the second reagents.

In the embodiment shown in FIG. 2, the data values of the stocked reagents may be transferred between the random access memory unit 37 and non-volatile memory unit 36 at any time. Therefore, prior to switching off the electric power supply after the completion of a series of the analysis or upon an occurrence of any malfunction, the data values stored in the memory unit 37 are transferred into the non-volatile memory unit 36 and stored therein. When the power supply is switched on again, the data values stored in the non-volatile memory unit 36 are transferred to the memory unit 37. In this manner, a user needs not to reset residual amounts of the reagents every time the power supply is switched on. It should be noted that the transfer of the data values between the memory units 36 and 37 may be effected automatically in response to the switching on and off of the power supply. Further, in order to prepare for a sudden breakdown of the power supply, the data values stored in the memory unit 37 may be always transferred to the non-volatile memory unit 36.

In a modified embodiment of the reagent managing system according to the invention, there are provided a plurality of reagent storage units and reagents are classified into a plurality of groups in accordance with the frequency of using them, each classified groups of reagents being set in respective reagent storage units. This construction is quite preferable for an analyzer performing a number of test items and is sometimes called an analyzer of round exchange type. Then the random access memory unit 37 and non-volatile memory unit 36 may comprise a number of storing areas which is equal to the number of test items within a single round multiplied by the number of rounds. Further identification codes are applied to respective reagent storage units and reagent tanks set therein. The analyzer 31 comprises a mechanism for automatically detecting the identification codes of a reagent storage unit which is just set in the analyzer 31, and the detected identification codes are supplied to the computer 32. Then the test items and the data values of reagents corresponding to the detected round are displayed on the display unit 38 in the same manner as that explained above.

In this modified embodiment, even if the analyzer can perform a number of test items by exchanging the rounds, amounts of all reagents to be used in all test items can be managed effectively and therefore, any cumbersome operation for setting amounts of reagents at the time of round exchange can be completely removed.

In a further modified embodiment of the reagent managing system according to the invention, the alarm threshold values in the form of the numbers of tests for respective reagents are entered from the input unit 35 into the computer 32 as illustrated in FIG. 3. The actual values of the numbers of tests are always compared with the threshold values and when they become equal to each other, an alarm is generated. That is to say, the number of tests for a reagent is reduced by one every time a relevant reagent is used and the reduced number is compared with a related threshold number. When the reduced number becomes equal to the alarm threshold number, a buzzer is generated and the displayed number of tests for the relevant reagent is lit on and off or is displayed in a reversed manner. Therefore, a user can be aware of the shortage of reagent before the reagent will be actually consumed completely, and thus the user can supplement the reagent or exchange the relevant reagent tank by a new one. In this manner, any abnormal or useless analysis can be effectively prevented.

If the alarm threshold number is set to a relatively small one, a reagent may be utilized efficiently, but an actual amount of the reagent remained in a reagent tank might be smaller than a displayed value due to errors in reagent delivery, evaporation, etc. Then at the time of producing the alarm, the reagent has been smaller than the threshold volume and therefore, useless analysis might be conducted. In order to avoid this, when the alarm is generated, an analysis of a relevant test item may be temporarily stopped. In this case, when a user supplements the reagent or exchanges the reagent tank by a new one after the completion of the analysis and an amount of the supplemented reagent is entered into the computer with the aid of the input unit 35, the stop of the analysis of the relevant test item may be automatically released. Further, the alarm indication on the display unit 38 may be restored into an ordinary display after releasing the stop condition.

In the above embodiments, the number of tests for a reagent is reduced by one every time the relevant reagent is used once. But the number of reagent delivery may be accumulated. In this case the alarm threshold number may be set as the number up to which the reagent delivery may be effected safely, and when the accumulated number becomes equal to the alarm threshold value, an alarm may be generated.

As explained above in detail, the invention can be easily and economically practiced by merely adding the non-volatile memory to the known analyzer which already comprises the computer, keyboard, display device. Moreover, actual amounts of the reagents set in the analyzer can be reliably managed without checking the reagents and entering the data about the residual amounts of reagents every time the electric power supply is switched on. In this manner, the present invention can provide the automatic chemical analyzer in which the management of reagents can be performed economically and easily.

What is claimed is:

1. A system for managing at least one reagent set in a reagent storing section of an automatic chemical analyzer, comprising:

means for setting values representing total volume amounts of respective reagents initially set in the reagent storing section;

first storing means comprising a random access memory for storing the values entered by said setting means;

means for displaying the values stored in said first storing means; and second storing means including a non-volatile memory for storing the values stored in the first storing means;

said means for setting values further comprising a values changing means, responsive to each delivery of an aliquot part of a particular reagent set in the reagent storing section into a reaction vessel, for changing a value related to this reagent by one unit by subtracting a volume of said aliquot part from said initial total volume of said particular reagent and for providing a thus changed value to the first storing means to be stored therein and to be displayed on the displaying means.

2. A system according to claim 1, wherein the values stored in the first storing means are transferred to the second storing means and are stored therein every time an electric power supply is switched off, and the values stored in the second storing means are transferred to the first storing means and are stored therein every time the electric power supply is switched on.

3. A system according to claim 1, wherein said values stored in the first storing means are transferred to the second storing means and are stored therein, and every time an electric power supply is switched on, the values stored in the second storing means are transferred to the first storing means and are stored therein.

4. A system according to claim 1, wherein said non-volatile memory comprises one of floppy disc storage, hard disc storage, bubble memory, core memory and battery backed-up CMOS.RAM.

5. A system according to claim 1, wherein each of said values is always compared with respective one of alarm threshold values corresponding to the respective reagents, and when a value of a reagent becomes equal to an alarm threshold value related to the relevant reagent, an alarm is generated.

6. A system according to claim 5, wherein said alarm is generated by changing a display of the related reagent displayed on said displaying means.

7. A system according to claim 5, wherein said alarm is generated by producing audible sound.

8. A system according to claim 1, wherein a plurality of reagent storages having identification codes are exchangeably set in the reagent storing section, and values representing amounts of a plurality of reagents installed in each reagent storages are processed under the control of the identification codes when a round is exchanged.

9. A system for managing at least one reagent set in a reagent storing section of an automatic chemical analyzer, comprising:
means for setting values representing amounts of respective reagents initially set in the reagent storing section;
first storing means comprising a random access memory for storing the values entered by said setting means;
means for displaying the values stored in said first storing means; and
second storing means including a non-volatile memory for storing the values stored in the first storing means;
said means for setting values comprising values changing means, responsive to each delivery of an aliquot part of a reagent set in the reagent storing section into a reaction vessel, for changing a value related to this reagent by one unit and for providing a thus changed value to the first storing means to be stored therein and to be displayed on the displaying means, wherein said value representing an amount of a reagent is the number of tests able to be performed by the reagent set in the reagent storing section, and every time the reagent is delivered, the number of tests is reduced by one.

10. A system according to claim 9, wherein the values stored in the first storing means are transferred to the second storing means and are stored therein every time an electric power supply is switched off, and the values stored in the second storing means are transferred to the first storing means and are stored therein every time the electric power supply is switched on.

11. A system according to claim 9, wherein said values stored in the first storing means are transferred to the second storing means and are stored therein, and every time an electric power supply is switched on, the values stored in the second storing means are transferred to the first storing means and are stored therein.

12. A system according to claim 9, wherein said non-volatile memory comprises one of floppy disc storage, hard disc storage, bubble memory, core memory and a battery backed-up CMOS.RAM.

13. A system according to claim 9, wherein each of said values is always compared with respective ones of alarm threshold values corresponding to the respective reagents, and when a value of a reagent becomes equal to an alarm threshold value related to the relevant reagent, an alarm is generated.

14. A system according to claim 13, wherein said alarm is generated by changing a display of the related reagent displayed on said displaying means.

15. A system according to claim 13, wherein said alarm is generated by producing an audible sound.

16. A system according to claim 9, wherein a plurality of reagent storages having identification codes are exchangeably set in the reagent storing section, and values representing amounts of a plurality of reagents installed in each reagent storages are processed under the control of the identification codes when a round is exchanged.

* * * * *